(12) United States Patent
Rattner et al.

(10) Patent No.: US 12,211,220 B2
(45) Date of Patent: Jan. 28, 2025

(54) SYSTEMS AND METHODS FOR USE AND ALIGNMENT OF MOBILE DEVICE ACCESSORIES FOR MOBILE DEVICES

(71) Applicant: FITSKIN INC., Toronto (CA)

(72) Inventors: Sergio Rattner, Toronto (CA); Justinas Vilimas, Vilnius (LT)

(73) Assignee: FITSKIN INC., Toronto (CA)

( * ) Notice: Subject to any disclaimer, the term of this patent is extended or adjusted under 35 U.S.C. 154(b) by 618 days.

(21) Appl. No.: 17/431,691

(22) PCT Filed: Feb. 19, 2020

(86) PCT No.: PCT/CA2020/050216
§ 371 (c)(1),
(2) Date: Aug. 17, 2021

(87) PCT Pub. No.: WO2020/168428
PCT Pub. Date: Aug. 27, 2020

(65) Prior Publication Data
US 2022/0138972 A1 May 5, 2022

Related U.S. Application Data

(60) Provisional application No. 62/807,553, filed on Feb. 19, 2019.

(51) Int. Cl.
G06T 7/30 (2017.01)
A61B 5/00 (2006.01)
(Continued)

(52) U.S. Cl.
CPC .............. *G06T 7/30* (2017.01); *A61B 5/0077* (2013.01); *A61B 5/441* (2013.01); *A61B 5/6898* (2013.01);
(Continued)

(58) Field of Classification Search
CPC . G06T 7/30; G06T 7/0012; G06T 7/11; G06T 7/70; G06T 2207/20132;
(Continued)

(56) References Cited

U.S. PATENT DOCUMENTS

2012/0023642 A1    9/2012 O'Neill
2012/0236425 A1*   9/2012 O'Neill .................. G02B 7/14
                                                    359/827
(Continued)

FOREIGN PATENT DOCUMENTS

JP      2010160286 A        7/2010
JP      2014131121 A   *    7/2014   ............. H04N 5/232
WO    WO-2017181293 A1 *   10/2017   ........... A45D 44/005

*Primary Examiner* — Nhan T Tran
(74) *Attorney, Agent, or Firm* — Jenna L. Wilson; Wilson Lue LLP (firm)

(57) ABSTRACT

A method for aligning a removably attachable skin analysis device to a mobile device is disclosed. The method is particularly applicable to skin analysis devices comprising a housing that defines a housing aperture, the housing aperture comprising a housing aperture center and wherein the housing aperture is centered on a camera of the mobile device when the skin analysis device is in an aligned position, and the method includes capturing, with the camera, a current position image, wherein the current position image comprises at least a portion of the housing aperture, processing the current position image to determine if the current position is the aligned position and communicating a message from the processing.

19 Claims, 6 Drawing Sheets

(51) Int. Cl.
  *G06T 7/00* (2017.01)
  *G06T 7/11* (2017.01)
  *G06T 7/70* (2017.01)
  *H04N 23/60* (2023.01)
(52) U.S. Cl.
  CPC .............. *G06T 7/0012* (2013.01); *G06T 7/11* (2017.01); *G06T 7/70* (2017.01); *H04N 23/64* (2023.01); *G06T 2207/20132* (2013.01); *G06T 2207/30088* (2013.01)
(58) Field of Classification Search
  CPC ........ G06T 2207/30088; A61B 5/0077; A61B 5/441; A61B 5/6898; A61B 5/442; A61B 5/443; A61B 5/444; A61B 5/445; A61B 5/743; A61B 5/0022; A61B 5/744; A61B 5/103; H04N 23/64; G03B 17/565; G03B 17/566; G03B 17/56
  See application file for complete search history.

(56) References Cited

U.S. PATENT DOCUMENTS

| | | | |
|---|---|---|---|
| 2016/0098847 A1* | 4/2016 | Crnokrak | A61B 5/02055 345/593 |
| 2018/0048793 A1 | 2/2018 | Gross | |
| 2018/0106676 A1 | 4/2018 | Jang | |
| 2018/0357803 A1* | 12/2018 | Zhang | G06T 11/60 |
| 2019/0125249 A1* | 5/2019 | Rattner | A61B 5/444 |
| 2019/0343396 A1 | 11/2019 | Khosravi et al. | |

* cited by examiner

SYSTEMS AND METHODS FOR USE AND ALIGNMENT OF MOBILE DEVICE ACCESSORIES FOR MOBILE DEVICES

CROSS-REFERENCE TO RELATED APPLICATIONS

This application claims priority from U.S. Provisional Application No. 62/807,553, filed on Feb. 19, 2019, the contents of which are herein incorporated by reference.

BACKGROUND

The ability to determine the best skin care products to use and the cosmetics color that best matches your skin are two of the biggest challenges in the beauty industry. These challenges are compounded when shopping online. Without the experience of a dermatologist or trained professional, and a color calibrated screen, it's almost impossible to make the best purchase decision.

Prior devices to solve at least some of these problems had to be specifically designed to fit a particular smart device, or are integrated as one device that includes the camera, processor, wireless transmitter, and screen. These approaches reduce flexibility and increase costs.

This invention solves both problems, with an easy to use low-cost device. The device works with many computing devices, such as an Apple iPhone, Samsung Tablet, laptop PC, desktop PC. It can also be attached to almost any digital camera.

For some mobile accessories, alignment may be crucial for proper performance—even a small deviation from an aligned position can render the mobile accessory ineffective. As such, proper alignment is crucial. At the same time, flexible hardware, that can be attached and removed easily for satisfactory user experience, may not include alignment mechanisms or approaches that are purely hardware-based—hardware and algorithms may be used together. But mobile devices may have limited resources (processing power, memory, screen size, and the like) and the functions of the mobile accessory may be only a small focus of what the mobile device is performing for a user. So any algorithmic or software portions of the solution to a unique mobile accessory, that is able to perform unique functions based on a unique design, that can also be removably attached to a mobile device, must use limited resources of the mobile device to be aligned properly. Such a need thus remains.

FIELD OF THE INVENTION

This invention relates to an apparatus and method for measuring various skin attributes and in particular an apparatus that can fit on any smartphone, tablet, or computing device with a built-in camera.

SUMMARY OF THE INVENTION

There is a device for enabling measurements using smart devices, the device comprising a tensioned clip that attached to a smart device, and a component housing to house one or more electronic components.

The device may further comprise a guide opening, located opposite the housing, that may allow a screen guide, on a screen of the smart device, to be seen when the smart device is attached and secured to the smart device.

There is also a method for enabling measurements using smart devices using a device, the method comprising: attaching the device on the smart phone such that a housing of the device is located proximate to a camera on a back side of the smart device and adjusting the device such that a screen guide on a screen of the smart phone is visible through a guide opening of the device.

There is a method for aligning a removably attachable skin analysis device, the skin analysis device comprising a housing that defines a housing aperture, the housing aperture comprising a housing aperture center and wherein the housing aperture is centered on a camera of the mobile device when the skin analysis device is in an aligned position, the housing further comprising skin analysis components that perform skin analysis, the method comprising:
 observing the skin analysis device in a current position on the mobile device;
 capturing, with the camera, a current position image, wherein the current position image comprises at least a portion of the housing aperture;
 processing the current position image to determine if the current position is the aligned position; and
 communicating a message from the processing.
The processing may further comprise:
 performing halo processing; and
 if the halo processing is successful:
  using bottom surface micro processing to confirm the halo processing.
The camera may have a field of view further comprising a field of view center and wherein the processing may further comprise:
 locating the housing aperture center in the current position image;
 checking if the housing aperture center is centered on the field of view center in the current position image; and
 returning a success message if the housing aperture center is centered on the field of view center and a failure message if the housing aperture center is not centered on the field of view center.

The housing aperture may have a circular bottom surface, and a portion of the housing aperture in the current position images may comprise a set of arc portions of the circular bottom surface and the locating may comprise using the set of arc portions to determine the housing aperture center.

The locating may comprise performing halo processing.

If the housing aperture center is not centered on the field of view center in the current position image, the checking may further comprise:
 computing an adjustment, using the located housing aperture center, to apply to the skin analysis device to move the skin analysis device from the current position to the aligned position; and
 wherein the failure message further comprises the adjustment.

The calculating may further comprise cropping the current position image to normalize for the camera's field of view.

The processing may further comprise:
 macro processing the current position image for a misalignment visual indicator; and
 if a misalignment visual indicator is found then returning a failure message that further comprises an adjustment to remove the misalignment visual indicators from the current position image.

The method may further comprise displaying, on the screen of the mobile device, the message.

The method may further comprise performing joint functionality, if the message is a success message.

There is further a method for preparing an alignment dependent mobile device accessory (mobile device accessory) in an aligned position on a mobile device, the method comprising:

observing the mobile device accessory in a current position, removably attached to the mobile device, the current position being an unknown alignment position;

obtaining a current position image from a camera of the mobile device, the current position image comprising an image of at least a portion of the mobile device accessory in the current position;

processing the current position image to determine if the current position is the aligned position; and communicating a message from the processing.

If the current position is not the aligned position then the processing may further comprise:

calculating an adjustment to apply to the mobile device accessory to move the mobile device accessory from the current position to the aligned position and the message further comprises the adjustment.

The processing may further comprise:

macro processing the current position image for a misalignment visual indicator; and if a misalignment visual indicator is found then the message further comprises an adjustment to remove the misalignment visual indicators from the current position image.

The method may further comprise:

showing, on a screen of the mobile device and before the observing, an alignment guide to assist in placing the mobile accessory in the current position.

The alignment guide may have a shape of a base connector of a mobile device accessory, wherein the base connector is to touch the screen in the location and orientation of the alignment guide.

The alignment guide's shape and location may vary for each mobile device.

The communicating may further comprise displaying, on the screen of the mobile device, a current position indicator that represents the current position relative to the aligned position, wherein the current position indicator may be static in location but varies depending on how close the current position is to the aligned position.

There is also a system for skin care analysis comprising:

a skin analysis device, removably attachable to a mobile device, the skin analysis device comprising a housing that defines a housing aperture, the housing aperture comprising a housing aperture center and wherein the housing aperture is centered on a camera of the mobile device when the skin analysis device is in an aligned position, the housing further comprising skin analysis components that perform skin analysis; and the mobile device, further comprising a screen and a camera, the mobile device configured to:

capture, with the camera, a current position image, wherein the current position image comprises at least a portion of the housing aperture;

process the current position image to determine if the current position is the aligned position; and communicate a message from the processing.

The camera may have a field of view further comprising a field of view center and wherein the processing may further comprise:

locating the housing aperture center in the current position image;

checking if the housing aperture center is centered on the field of view center in the current position image; and returning a success message if the housing aperture center is centered on the field of view center and a failure message if the housing aperture center is not centered on the field of view center.

The housing aperture may have a circular bottom surface, and a portion of the housing aperture in the current position images may comprise a set of arc portions of the circular bottom surface and the locating may comprise using the set of arc portions to determine the housing aperture center.

If the housing aperture center is not centered on the field of view center in the current position image, the checking may further comprise:

computing an adjustment, using the located housing aperture center, to apply to the skin analysis device to move the skin analysis device from the current position to the aligned position; and wherein the failure message further comprises the adjustment.

The calculating may further comprise cropping the current position image to normalize for the camera's field of view.

The processing may further comprise:

macro processing the current position image for a misalignment visual indicator; and if a misalignment visual indicator is found then returning a failure message that further comprises an adjustment to remove the misalignment visual indicators from the current position image.

The mobile device may be further configured to display, on the screen of the mobile device, the message.

The mobile device may further be configured to perform joint functionality, with the skin analysis device, if the message is a success message.

The skin analysis device may further comprise a base, hingedly attached to the housing at an end of the base and an end of the housing, and wherein the base and the housing contact the mobile device, on opposite sides of the mobile device, such that that skin analysis device is pressuredly attached to the mobile device.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE PREFERRED EMBODIMENTS

Figure 1A:
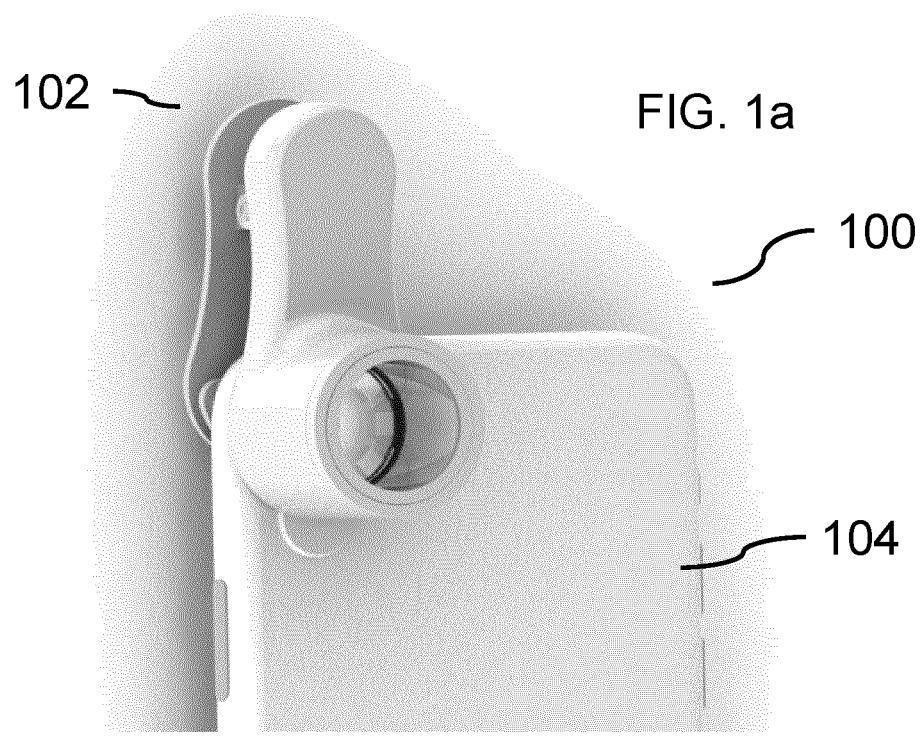
FIGS. 1a-b illustrate aspects of an exemplary mobile device and mobile accessory, and related system, according to an embodiment of the present invention.

Broadly, the invention as herein described is a mobile accessory that attaches to a mobile device and performs some form(s) of functionality, that may be performed in conjunction with the mobile device. The alignment of the mobile accessory may be important for proper execution of the function of the mobile accessory. Mobile accessories may be uniquely shaped and may provide unique functionality, such as one or more skin analysis actions like being part of capturing images of a human face to assess moisture, pores and the like (for example jointly with mobile device components). Images and other measurements are stored, compared to other samples and used to recommend products to assist with skin care. While proper alignment is vital, the mobile device and mobile accessory may have limited computing resources, such that it is desirable to determine proper alignment efficiently and not overburden elements of system 100.

As used, and further described herein, the following terms have the following meanings:
- (a) Alignment dependent mobile device accessory: a mobile device accessory that requires proper alignment on a mobile device to perform its functionality, where the alignment may need to be substantially perfect or the functionality will be nearly useless.
- (b) Back side: the side of an electronic device that typically faces away from the user when the electronic device is being used by its user and may have a back camera.
- (c) Electronic device or mobile device: a device, having at least one camera (and preferably at least one back camera), onto which a mobile device accessory can be attached, that may preferably be mobile (such as mobile phones and tablets), exemplary electronic devices including smart phones, tablets, digital cameras, personal computers, televisions and the like.
- (d) Electronic device accessory or mobile device accessory: an accessory that can be removably attached to a mobile device, which may include a skin analysis device.
- (e) Front side: the side of an electronic device that typically faces towards the user when the electronic device is being used by its user, and may have a front camera and a screen.
- (f) Image: Unless specified otherwise, references herein to image(s) refer to digital images that can be represented by digital data capable and can be manipulated and processed by electronic devices and computers (such as an app);
- (g) Joint functionality: functionality performed jointly by the mobile device and mobile device accessory/alignment dependent mobile device accessory;
- (h) Skin characteristics: one or more characteristics of skin (including hair), such as color, moisture, oiliness, elasticity, and the like.
- (i) Skin characteristic measurement assisters: components that assist a skin characteristic measurement device in taking a skin care measurement. These may either be generally thought of as passive (ie not requiring control by the electronic device or skin analysis device) or active (requiring control etc by the electronic device, such as light source board, and vibration motor).
- (j) Skin characteristic measurement device: a component that takes skin analysis actions, either under its own control or the control of another component. These may either by on MD 104, MA 102, or separate therefrom. Each may take, or be part of taking, multiple skin analysis actions, skin analyses, skin analysis calibrations and skin analysis measurements.
- (k) Skin analysis/analyses: one or more analyses of one or more skin characteristics.
- (l) Skin analysis action: an action that leads to or results in some portion of skin analysis occurring, such as skin analysis measurements, exemplary skin analysis actions including taking a picture, reading a moisture sensor, testing elasticity via images or recordings, and the like.
- (m) Skin analysis calibrations: calibrating one or more aspects of the skin analysis device and/or the electronic device, to allow accurate skin analyses, exemplary skin analysis calibrations including light normalizing for exposure and color temperature (where both may be accomplished using a transformation function for color correction)
- (n) Skin analysis device: the device, according to aspects of the present invention, that is removably attachable to an MD 104 and may have one or more skin characteristic measurement devices, or skin characteristic measurement assisters.
- (o) Skin analysis measurements: measurements of one or more skin characteristics, including acquiring moisture readings, images for lines/wrinkles/pores, elasticity readings, skin color, and the like, any of which may be represented as 'scores'—either absolute, relative or averages—ie a pore score, a relative line score, a color, etc.
- (p) Skin analysis processings: processing of one or skin analysis measurements, such as by performing image processing on an image.
- (q) Skin analysis recommendations: using one or more results of one or more skin analyses, and characteristics of one or more skin care products, to recommend an appropriate skin care product for a user.
- (r) Skin care products: products that assist with one or more skin care characteristics, such as moisturizers, wrinkle creams, cosmetics (such as foundation and blush), and the like.
- (s) Skin care product manufacturers: makers, manufacturers, distributors, brands and brand owners of skin care products.
- (t) Skin care product characteristics: attributes of a particular skin product, which may include a product's color, moisturizing ability, line reducing ability, and the like.
- (u) Skin care updates: these may include information relevant to skin care that may come from external sources. For example, weather (clouds, sun, high UV, snow) may come from weather sources (not shown, but known to those in the art).
- (v) Skin characteristic: characteristics of skin or body part, such as pores, spots, sensitivity (which may use polarized or other light spectrum to show blood vessels that are close to the surface of skin, which may result in 'redder' images, lines, elasticity, moisture, oil, acne, and skin color.
- (w) User/human user/subject, person: the person using the skin analysis device and/or who is the subject of the skin characteristic sample, as the case dictates.

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations.

All of the implementations described below are exemplary implementations provided to enable persons skilled in the art to make or use the embodiments of the disclosure and are not intended to limit the scope of the disclosure.

It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings.

The flowchart and block diagrams in the flow diagrams illustrate the architecture, functionality, and operation of possible implementations of systems, methods, and computer program products according to various embodiments of the present invention. In this regard, each block in the flowchart or block diagrams may represent a module, segment, or portion of code, which includes one or more executable instructions for implementing the specified logical function(s). It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions. These computer program instructions may also be stored in a computer-readable media that can direct a computer or other programmable data processing apparatus to function in a particular manner, such that the instructions stored in the computer-readable media produce an article of manufacture including instruction means which implement the function/act specified in the flowchart and/or block diagram block or blocks.

Figure 1B:
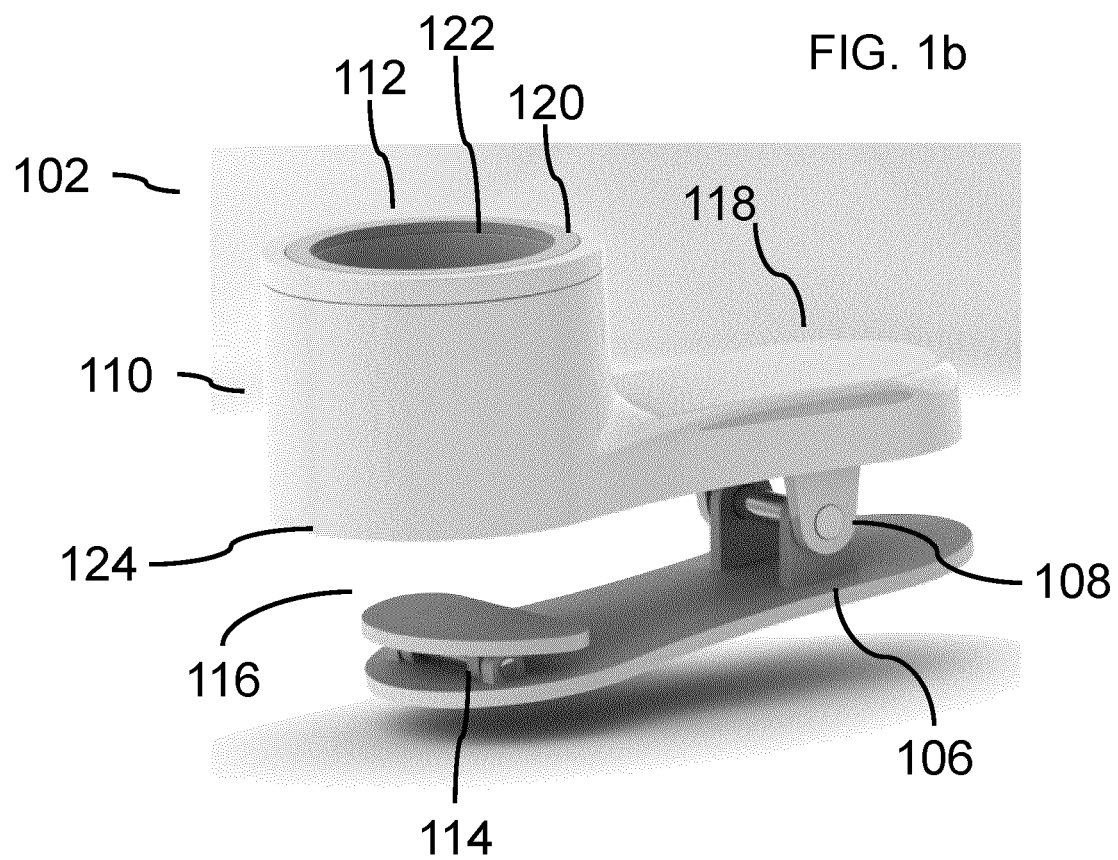
Figure 2:
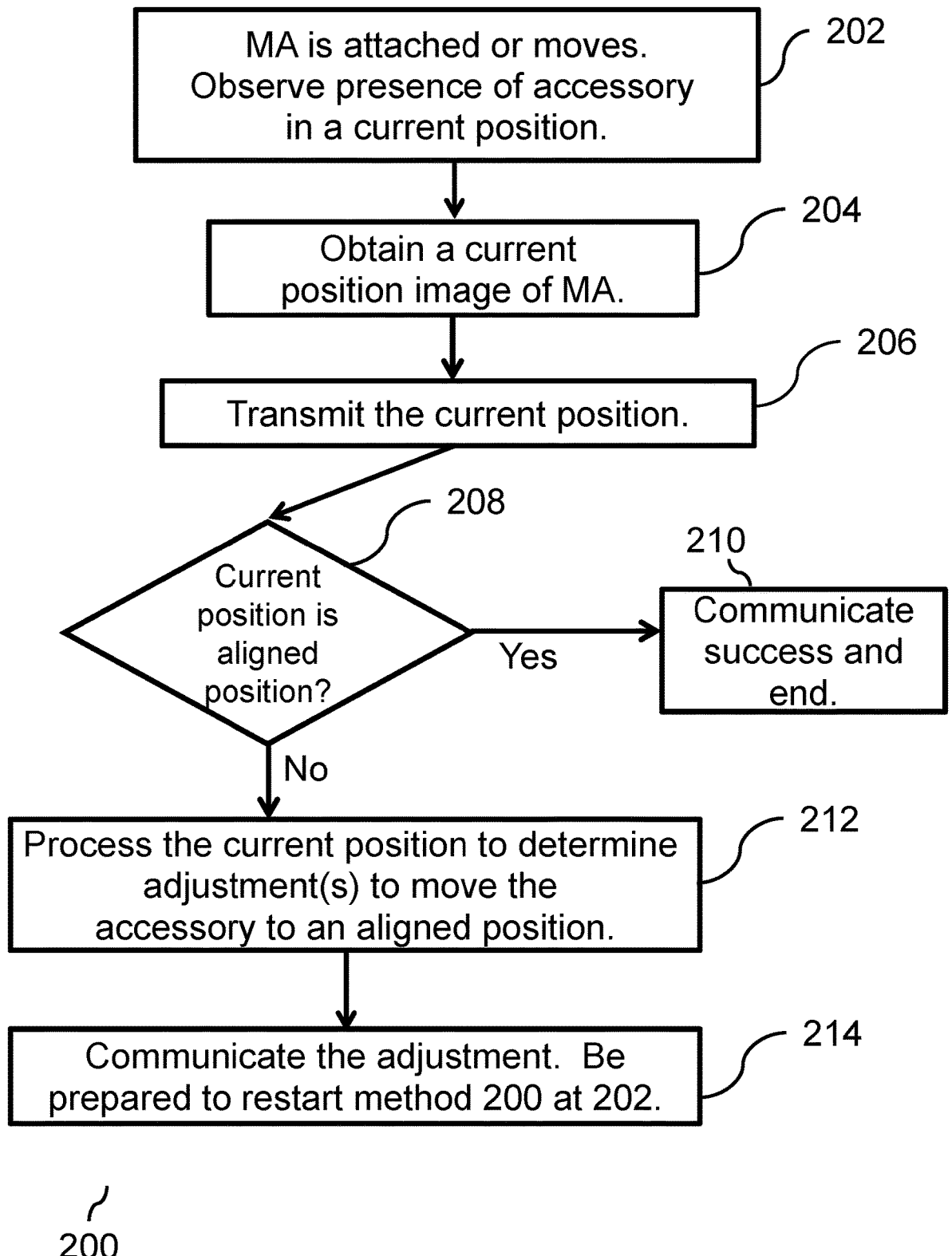
FIG. 2 is a method for aligning a removable mobile accessory with a mobile device according to an aspect of the present invention.

FIG. 1a illustrates aspects of a system 100, comprising mobile device accessory (MA) 102 and mobile device (MD) 104. FIG. 1b illustrates MA 102, further comprising accessory base (base) 106 hingedly attached to accessory body (body) 118 by hinged attachment 108, base 106 further comprising base contact 116 hingedly attached to base 106 via hinged connector 114, and body 118 further comprising accessory housing (housing) 110 which may further comprise accessory housing components (components) 112, housing contact/bezel 120 and housing aperture 122.

System

System 100 may allow a user to connect or attach, and position, MA 102 on MD 104 such that it is in an aligned position, allowing MA 102 to operate optimally—all of such as may be more thoroughly described herein. Despite the preference for the aligned position to be substantially perfectly aligned (for example the center of housing aperture lining up exactly with the center of the field of view of a camera of MD 104) there may be some tolerance to imperfect alignment still constituting being in an aligned position—particularly based on the adjustments to performing the functionality (skin analysis, joint functionality and the like), as described herein.

MD 104

MD 104 may be a mobile phone such as an iPhone™ or Android™ phone, a tablet, laptop, or other computing device. MD 104 may have one more components thereof, such as one or more cameras (with at least one on a back side of MD 104), and other components as are common for such devices, such as flash 8 for a camera, power and volume buttons, a motor to cause vibration ("vibration motor", interior to MD 104), screens such as 308, processors, storage/memory, and the like (some or all of which MA 102 may also have, in order to perform processing, store instructions and/or data, and the like). Some of such components may have visual or physical aspects thereto, that may be visible or present on the exterior surface of MD 104 ("visible components"). Other components may be internal to MD 104, such as GPS transceivers ("internal components") but may have requirements for external surfaces of MD 104 to function properly (such as not blocking GPS or other wireless signals).

MD 104 may comprise expensive and powerful components (including but not limited to processors, storage/memory, camera and the like). However, such components may not be suited to be skin characteristic measurement devices, or skin characteristic measurement assisters, without other skin characteristic measurement devices or skin characteristic measurement assisters. For example, camera may have good resolution but may not have adequate traits (such as optical zoom or magnification) to enable capturing images that are suitable for skin characteristics and skin characteristic samples, and also images of MA 102 to perform alignment. Hence, as described herein, skin characteristic measurement assisters (on MA 102 and/or MD 104) may be employed, and other skin characteristic measurement devices may be employed).

MD 104 may have an operating system that provides access to various application programming interfaces ("API"). Such API allow apps on MD 104 to 'call' the API and thus access various functionality of MD 104 (such as camera 12, controlling a vibration motor, turning on an electronic device light source such as flash 8 or controlling its operation when performing skin care actions, and the like).

Figure 5A:
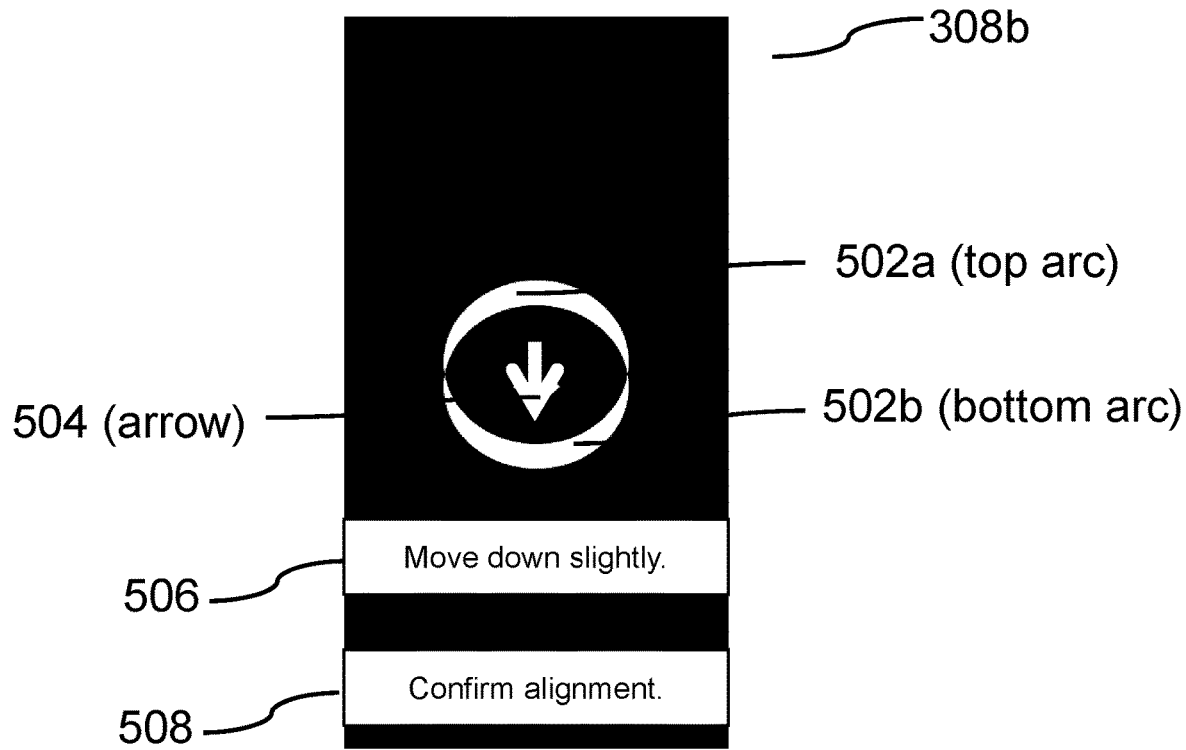
FIGS. 5a-b and 6 illustrate screenshots of an app for a mobile device according to an aspect of the present invention.
Figure 5B:
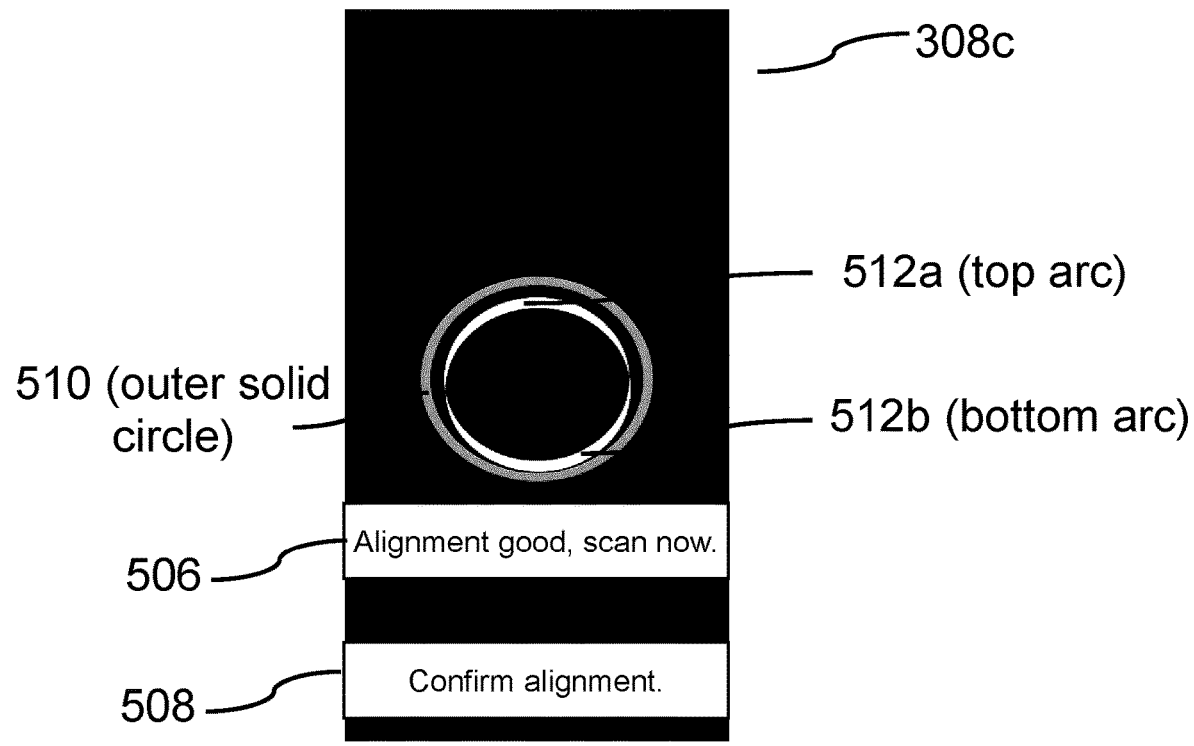

MD 104 may have software located thereon (such as an 'app') as is known, that may be obtained and installed from an 'app store'. The app according to an embodiment of the present invention may be accessed on MD 104 to perform functionality as described herein and may be a human user's primary way to interact with MD 104 (in terms of accessing functions described herein) and MA 102. App may be able to access various features and components of MD 104, such as displaying various user interfaces 308, with various user interface components (such as shown and described with respect to FIGS. 3 and 5). In particular, app may receive inputs from users, and provide signals to MA 102 (for example to take a moisture sensor reading, turn on light sources, and the like). The app may also be able to access storage located on MD 104, such as to store data and instructions, as described herein. The app may also be able to perform communications between MD 104 and MA 102, and one or more networks.

MA 102

MA 102 (a mobile device accessory or more simply a mobile accessory) may be an accessory that is attached to MD 104. Such attachment may be accomplished in any number of ways, though preferably such attachment is i) removable, ii) adjustable and iii) attachment and removal is fast to perform. MA 102 may have a purpose for a user of MD 104; such purpose may be related to purposes of MD 104 or may be separate therefrom. Preferably, MA 102 has an optimal position for attachment to MD 104—where MA 102 is able to perform its purpose(s) most effectively. Such position may be referred to as an aligned position. In an embodiment such aligned position may refer to a part of body 118 being aligned with a feature on the back side of MD 104 (such as a back camera). Preferably, MA 102 can be photographed by MD 104 when MA 102 is attached thereto, resulting in a current position image of MA 102. Preferably, a current position image can be analyzed, such as by MD 104, to i) determine or compute a current position of MA 102 relative to MD 104, which may assist in getting MA 102 into an aligned position and ii) determine one or more adjustments (translating, rotating, tightening, and the like) to move MA 102 from its current position to an aligned position. Preferably the size and shape of MA 102 can be used for various MDs 104 (ie one model or design of MA 102 working for various mobile phone sizes, camera locations, and the like—subject to the possible adjustments to system 100 described herein, to account for such differences in MDs 104).

Exemplary MA 102 may be as skin analysis device, such as shown in FIG. 1b. MA 102 and described herein.

Exemplary MA 102 may be an alignment-dependent mobile accessory and/or may perform joint functionality, as may be described herein.

MA 102 may further comprise base 106 and body 118. Such may be attached by a hinge system, such as hinged attachment 108, at an end of base 106 and an end of body 118 (or housing) resulting in base 106 being in pressured contact (via base contact 116) with one side of MD 104 (such as a front side) and body 118 being in pressured contact (via housing contact 120, or an outer ring 126 of the remote end of housing 110 from MD 104) with the other side of MD 104 (such as a back side) such that MA 102 is pressuredly attached to MD 104. Base 106 and body 118 may be connected together in many different ways such that base 106 and body 118 touch MD 104 and prevent MA 102 from falling off or moving in normal operation. Such pressured contact may be one form of a connection to MD 104 that may be referred to as removably attached. Clips, magnets and other such approaches may be removably attached, whereas screwed connections may be more permanent and less likely to be considered removably attached. And MA 102 need not be on both sides of MD 104, but could be just on one side (for example using an adhesive, magnet, or other approach for removably attachment to one side of MD 104).

Preferably both base 106 and body 118 may be substantially parallel to the front or back side of MD 104, when in a current position and aligned position. However, more likely, body 118 and/or body housing 110 need to be substantially parallel to the back of MD 104 and perpendicular to the camera lens (such that aperture 122 of housing 110 is parallel to a back camera). In such a situation base contact 116 may be substantially parallel to the front of MD 104 (allowing a solid pressure contact and connection to MD 104) though base 106 may not be parallel. This may be part of the design of hinged connector 114 and the hinged connection it creates between base 106 and base contact 116. A top surface of base contact 116 (the surface that will be in contact with MD 104), and a touch sensitive screen thereof, may be touch sensitive, such that MD 104 can sense the touch of base contact 116. Generally then base contact 116 is an example of an MA guiding element—an element of MA 102 that is in detectable contact with a screen (touchscreen) of MD 104 when MA 102 is approximately in the aligned position, and may be matched with an alignment guide on a screen to provide a user an initial guide for roughly where MA 102 should be placed. Although there may be other initial guides, such an approach may be preferred as such may be more accurate for a particular MD 104 than just a general guide—as further described herein. A preferred, and approximate, arrangement of the attachment of MA 102 to MD 104 can be seen in FIG. 1a.

While more permanent attachments (such as via screws, brackets, and the like) are possible, they may not be optimal for the user experience (for example then requiring MA 102 to be adjusted for each MD 104) even if they might reduce complexities of determining adjustments to reach an aligned position, as described herein.

Of course, it is to be understood that the mechanical details of hinged connector 114 and hinged attachment 108, and in fact of base 106 and body 118, may be adjusted to allow a solid connection with MD 104 when in an aligned position.

Body 118

Body 118 may further comprise accessory housing (housing) 110 which may further comprise components 112, housing contact or bezel 120 and housing aperture 122.

Housing 110 may comprise several components of MA 102, such as color calibrator, Bluetooth transceiver (embedded in a processor or separate therefrom), light source board, diffuser, moisture sensor, lens, one or more light sources and light-specific apertures and diffusers, calibration rings, a processor, storage, a battery, and the like, and housing 110 may form housing aperture 122.

Housing aperture 122 may be cylindrical, as defined by bezel 120. In reality bezel 120 may slightly narrow housing aperture 122, but given bezel 120 may be thin, the effect may be small (for example it may be thin enough that no matter how poorly placed MA 102 is on top of the camera a halo will still be present as the camera will not "see" or capture only bezel 120. When in an aligned position housing 110 may be attached to MD 104 such that light does not enter housing aperture 122 except through aperture hole at the end of housing 110 that is furthest from MD 104 and base contact 116, and light does not reach a back camera of MD 104 except through housing aperture 122. As such images taken with a camera of MD 104 may be of the best quality, and components 112 may be used to augment such images. For example, the images in 400a and 400b were taken using a skin analysis device that has a 30× magnification lens in housing 110. Such lens could be removed entirely, such that skin analysis device has other components that contribute to image-taking (such as UV lights) but not magnification. In such a case the images would not be magnified as with 400a and 400b; different techniques may be applied for alignment, though the bottom surface approach and halo approach, alone or combination, may still be used.

Housing 110 may be sized and shaped such that when MA 102 is in an aligned position, or close to an aligned position, a bottom surface of housing 124 (which may be a cylindrical or circular ring, depending on housing 110) may be in contact with MD 104 and at least partly visible in an image taken by a camera of MD 104. Of course, a bottom surface of housing 124 may be in other shapes, such as ovular, square or random. In addition, bottom surface 124 may be completely outside of the field of view of the camera taking the current position. This may mean different " " are used. For example, when the bottom surface is within the field of view but is not circular there may be other image processing and geometrical solutions to determine a center of the aperture. When bottom surface is not within the field of view then halo 412 may be used. Ultimately, what may be important is that the center of the image for the camera operating on its own lines up with the center of the image that enters via the aperture.

Housing 110 may further comprise a housing contact 120 that may be substantially in contact with the subject when skin analysis occurs and that may be of a material that is comfortable for a user.

Method 200

Method 200 is a method for aligning MA 102 on MD 104 such that MA 102 is in an aligned position. Portions, or all of, method 200 may be performed iteratively—for example in adjusting MA 102 originally or adjusting MA 102 if it happens to move and slip out of an aligned position.

Portions of method 200 may be performed by a user (such as implementing the adjustments—ie physically moving MA 102 pursuant to an adjustment message).

Method 200 may be implemented by various elements of system 100, alone or in combination. Parts of method 100 may be implemented or performed separately, together and in various orders (even if depicted as part of method 200 and in a particular order). Various portions of method 200 may be depicted in screenshots 308a-d, and with reference to images 400a and 400b, as described further herein.

Method 200 begins at 202 where MA 102 is attached to MD 104 (such as by a user) or moves out of an aligned position (for example by a bump of MD 104). Attaching may begin by a user placing MA 102 roughly over the camera. As such, system 100 may observe the initial current position. Such position is the current position, and is also an unknown position (generally a position that has not yet been determined to be in an aligned position or a misaligned position).

System 100 may be aware that MA 102 is to be attached or re-aligned. For example, a user may open an app that relates to MA 102. In such a case, an app screen, such as GUI 308a in FIG. 3, may be shown to a user to help in attaching MA 102. GUI 308a may comprise an alignment indicator or alignment guide 302 and an initial attachment message 304.

Alignment guide 302 may be shaped to match base connector 116 (and in particular the top, touch sensitive, side thereof) and located on GUI 308a such that if base contact 116 covers alignment indicator 302 then MA's 102 current position, when attached, will be somewhat close to the aligned position. As such alignment guide 302 may act as a rough guide to the proper positioning of MA 102 to achieve the aligned position (so a user may cover the camera with one part of MA 102 and then seek to align a second part—such as base connector 106—with alignment guide 302). Further, alignment guide may be thought of as an initial or rough guide—that may be secondary to the primary system to actually determine an aligned position—as may be further described herein. Alignment guide 302 may be established in the app and may vary for each MD 104. Of course adjusting GUI 308a of the app for a particular MD 104 (and its shape, size, location of its one or more cameras, and even characteristics of cases for MD 104) may take some time, but may be easier than designing different form factors for MA 102.

Initial attachment message 304 may simply tell the user to align the clip using alignment guide 302, or other messages aimed at guiding the user to get MA 102 in an aligned position efficiently.

At 204, method 200 continues to obtain a current position image of MA 102. This may be triggered by the app, for example in response to the app detecting the presence of base contact 116 on screen 308a. The current position image may be taken by a camera of MD 104, such as a back camera. The camera may actually be operating in video mode, and computing of alignment may be done on images in the video stream, at a rate of 30 images per second.

At 206 the current position image is transmitted to give immediate feedback that may be displayed on a screen or GUI of the app.

At 208, method 200 continues to determine if the current position is the aligned position. If not, then at 212 the current position image is processed to determine one or more adjustments that are required to move MA 102 into an aligned position with respect to MD 104. Steps 208 and 212 are shown separately, but may be performed substantially simultaneously. The result of 208 may be success message or a failure message for, example, indicating that there is alignment or not. If adjustments are computed such adjustments may be added to the failure message, for example.

Processing the current position image to determine if the current position is the aligned position can vary, for example based on the capabilities of the camera of MD 104 that is taking the image (resolution, video or not, frame rate, field of view, lighting) and features of MA 102 and housing 110—for example, what features of MA 102 will be in the current position image when MA 102 is in an aligned position ("aligned position present features"), and what aligned position present features can be used to determine if the current position is the aligned position ("aligned position guiding features"). Processing can also quickly detect the presence of unexpected and/or undesirable visual features that indicate misalignment ("misalignment visual indicators"), such as 402 in image 400a. Even if processing cannot determine conclusively what 402 is (ie processing does not determine 402 is part of housing 110), processing (and likely even macro processing) can determine that 402 is present and is a misalignment visual indicator. If misalignment visual indicators are detected then processing may end and an adjustment may be computed based on the location of the misalignment visual indicators (for example if it is in the bottom right corner of the current position image then the adjustment would generally be to move the MA 102 down and to the right, to remove the misalignment visual indicator from the current position image).

The aligned position present features, the aligned position guiding features, and misalignment visual indicators may all be known in advance for any particular combination of MA 102 and MD 104 (where such combinations may be individuals, or based on types of MAs and MDs; where different MDs are less likely to cause major changes in the features or misalignment visual indicators than different MAs). For example, sample images may be captured when a particular MA 102 type is in an aligned position—an example being image 400b, where four arc portions from bottom surface 122 are seen, views through housing aperture are seen (as in 406, 410, 412) and the corners of image 400 include only small portions outside of the four arc portions. As such, artificial intelligence (or machine learning, etc) may be used to determine alignment, if that leads to increased efficiency. An AI engine may be trained based on sets of aligned position images for a particular MA 102, particular MD 104, combinations of MA 102 with MD 104, or other training sets. In such cases the AI engine may be part of the app, or may be distributed across all app users, and may be implemented on a server and possibly distributed across all app users (as processing may need to happen on MD 104 given a user not wanting latency in using the app). In the embodiment shown in FIGS. 1a/b, 4a/b there is a circular lower surface that is at least partly visible in the field of view of the camera. As such there are arcs, from the lower surface, and a halo 410. Such may be the alignment position guiding features.

Although generally all of the aligned position present features and aligned position guiding features may be on one side of MA 102, and processed by a single camera of MD 104, this is not required and multiple cameras (even on other sides of MD 104) may be used. Beyond that, some processing may be performed not on the current position image— such as determining that base contact 116 has touched the screen remote, to some extent, from alignment indicator 302. In such a case MD's 102 ability to tell the location of a touch of its screen can be leveraged to avoid unnecessary processing of the current position image.

Processing may further be thought of as including alignment processing ("is the current position the aligned position") and adjustment computation ("what changes to the location of MA 102 need to be made to move from the current position to the aligned position"). Both alignment processing and adjustment computation may comprises one or more of macro processing and micro processing, as described herein.

Alignment processing may further be broken into macro alignment processing (typically that detects macro-misalignment indicators—obvious, or macro elements of an image that show misalignment and typically require less processing, which may include elements or patterns in the image, improper lighting, and the like) and micro processing (typically that identifies or detects micro-misalignment indicators—subtle, or micro elements of an image that show misalignment and typically require more processing, which may include finding aligned position guiding features and calculating if they are in the correct location and/or orientation). Macro versus micro can be adjusted to suit the system 100 and user experience. Given the limitations of system 100 (such as processing power, memory and like) and that users do not want alignment to take too long, it is preferable not to perform more computations than required to achieve the aligned position. So macro alignment processing may occur largely before micro processing, and if macro alignment indicates macro-misalignment then micro alignment processing may not be performed at all.

Similarly, adjustment computation may further be broken into macro adjustment computation (to identify or compute macro, or gross, changes to the position of MA 102 to move towards the aligned position) and micro adjustment computation (to identify or compute micro, or finer, changes to the position of MA 102 to move towards the aligned position). Macro versus micro can be adjusted to suit the system 100 and user experience. Similar considerations, as with alignment processing, mean that it is preferable not to perform more computations than required to achieve the aligned position, so macro alignment processing may occur largely before micro processing, and if macro alignment indicates misalignment then micro alignment processing would not be performed.

In one embodiment, such as shown in FIGS. 1*a*-1*b* and 5, housing 110 has a lower surface 124 that is shaped like a circle. When in an aligned position the center of the circle of housing aperture may be at, or proximate to, the center of the field of view of MD 104 camera that is taking the current position image (as shown by camera center crosshairs 608), substantial portions of lower surface 124 may be in the current position image and may be symmetrically in the current position image, and little or no portions of housing 110, other than lower surface 124, may be in the current image position. In such an example, the aligned position present features may include lower surface 124 and a center of housing aperture 122, while the aligned position guiding features may include the same elements and expressly exclude other parts of housing 110 or potentially any other than the aligned position present features (items or patterns that should not be in the current position image being referred to as "misaligned image sections", a macro-misalignment indicator). As is discussed in more detail herein, if the center of housing aperture 122 is substantially in the center of the field of view of the camera, and the lower surface of housing 124 is in the field of view, and symmetrically in the field of view, then MA 102 may be in an aligned position. Of course, determining the center of housing aperture 122 may need to be established, as there may be no way to automatically determine it. This will be further discussed herein.

Continuing with method 200, if at 208 the MA 102 is not in the aligned position then at 212 adjustment(s) are determined. As described herein, adjustments may be any one or more of translations, rotations, and the like. Adjustments may be macro adjustments or micro adjustments. Adjustments may be based on macro or micro processing, such that method 200 may only know macro adjustments (for example if only macro processing was done, to save battery life, processing power, memory, etc). Adjustments may be qualitative ("move MA up", "move MA up a bit", "rotate MA counterclockwise", "rotate clockwise and slide down a bit") or quantitative ("move MA down 0.2 inches", "rotate 20 degrees clockwise"). Although adjustments are to get MA 102 into an aligned position they also need to be actionable. So adjustments, not only the determination of adjustments but, importantly, the determination of what adjustment(s) to communicate (and how), depend on how the adjustments will be actioned. For example, if a user (a person) is going to implement the adjustment then preference may be to quantitative adjustments and communicated in a simple way, such as the large arrow, an adjustment indicator, 504, possibly with adjustment message 506, and possibly with action button 508 (which the user may push to continue to use MA 102—perform skin analysis for example—though when alignment is achieved the app may move directly to using MA 102. Such arrow could point, indicate a spin, etc. The size of adjustment indicator 504 could show the extent or magnitude of the desired adjustment (ie a small arrow indicating a small movement in a particular direction). If a computing system is actioning or implementing the adjustment then a quantitative adjustment may be more useful. Determining adjustments may also be made with an understanding of how they will be actioned and what will be most effective in getting MA 102 to an aligned position—so that if a person is actioning the adjustment(s) then adjustments may be macro, or at least not so detailed as to be an exact quantitative adjustment (which may require more processing power, battery and memory), which would not help the person actioning the adjustment.

In any event, at 212, one or more adjustments are determined. Then method 200 continues to communicate the adjustments. Communication of adjustment(s) may be via any type of message (visual, auditory, vibratory, etc) that may let a user know how to move MA 102 towards the aligned position. For example, adjustment indicator may be a graphical representation of the adjustment(s), which may be displayed on the screen.

Returning to method 200 at 208, if at 208 the current position is the aligned position then at 210 success may be communicated and method 200 may end, at which point MA 102 may be used to perform its functionality, and importantly, any joint functionality may now be performed as well. Although the current position may be the aligned position, the aligned position may have some tolerance or acceptable deviation, such that perfect alignment is not achieved. In such a case images taken for skin analysis (or other functionality, such as hair analysis and the like) may have some inherent imperfections. These may be corrected for in post-processing of the images when performing such functionality (noting, for clarity, that this is after method 200 ends), for example via sharpening, chromatic aberration, and distortion. To know how to perform this post-processing method 200 may refer to a library of reference images and select a reference image that has the "minor misalignment" that most closely approximates the measure misalignment in the present "substantially aligned position". So if the present aligned position is actually 0.003" too "high" then the filtering, from the reference image of "0.003" too high", will be applied in post-processing.

Of course, the library could be large, to cover all possible permutations, but may not need to be to add value. For example, the library of reference images may be developed by:
  (a) taking images of a grid at a multitude of possible misalignments, such as the following misalignments (though any number are possible):
    (i) MA 102 being too high, low, left and right (and perhaps combinations, such as high/left, high/right, low/left and low/right), from 0.001" too high to 0.01" too high, at increments of 0.001";
    (ii) MA being rotated from 0.5 degrees off to 5 degrees off, at increments of 0.5 degrees;
  (b) for each of the images, knowing the grid should have straight lines, apply filters to return the lines to being straight, and saving the filter techniques.

Communication of success may be via any type of message (visual, auditory, vibratory, etc) that may let a user know that MA 102 is now aligned. That may further signal that MA 102 is ready to be used. One example of communicating success may be seen in FIG. 5b, where a solid circle for aligned position indicator 510 is shown around top arc 512a and bottom arc 512b. In such case solid circle is an alignment indicator, and the arcs show the location of portions of bottom surface 122 of housing 110. As can be seen in comparing FIGS. 5a and 5b, top arc 502a and bottom arc 502b on GUI 308b are wider than top arc 512a and bottom arc 512b on GUI 308c. This shows that MA 102 was not aligned (FIG. 5a) and then became aligned (FIG. 5b)—so the arcs 412 and 512 may remain static in location on the screen, but they may vary (such as in color or thickness) to indicate how close to the aligned position the current position is (ie how much movement is required to reach the aligned position).

After 210 method 200 may end, with no particular expectation of restarting. After 214 method 200 may expect to restart after an adjustment has been made, for example. In practice this may mean that app is ready to trigger the obtaining of a current position image more quickly—for example largely in real time, on a timer, or periodically of some sort—whereas after 210 a less frequent image capture may occur (a different frequency of image capture) or there may not be an further image capture until functioning of MA 102 indicates misalignment.

Additional details are now provided in regard to the example depicted in some of the figures herein. MA 102 that is depicted in the figures has a housing 110 with a lower surface 124 that is shaped like a circle and such lower surface should be substantially the only features in the current position image other than halo 412 and subject 410 (when MA 102 is in an aligned position) and its center (housing aperture center) will be located in the center of the field of view of the camera (field of view center) in an aligned position. This is because MA 102 is a skin analysis device that is leveraging the camera and thus it needs to be substantially disposed directly over the center of the camera.

In practice, a user attaches MA 102 to MD 104 by spreading the base 106 from the body 118, applying pressure to both near hinged attachment 108. The user then views screen 308a and makes their best attempt to place base contact 116 over alignment guide 302, as instructed by initial attachment message 304.

Figure 4A:
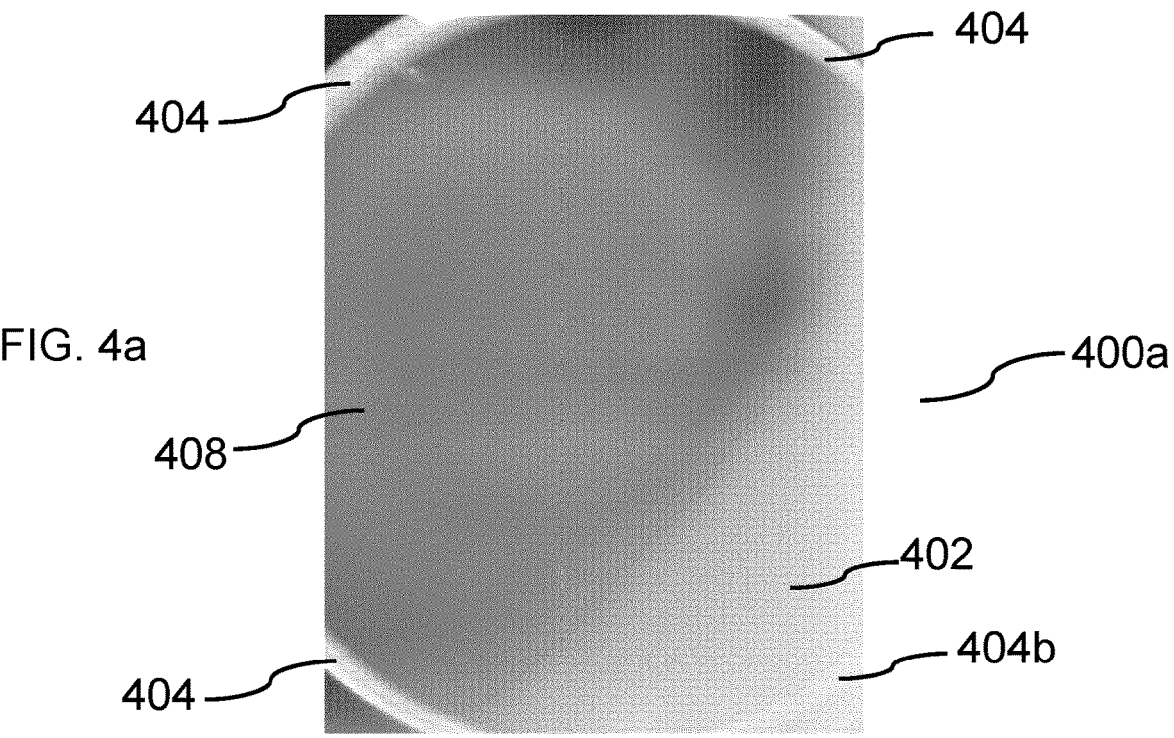
FIGS. 4a-b are exemplary current position images of a mobile accessory according to an embodiment of the invention.
Figure 4B:
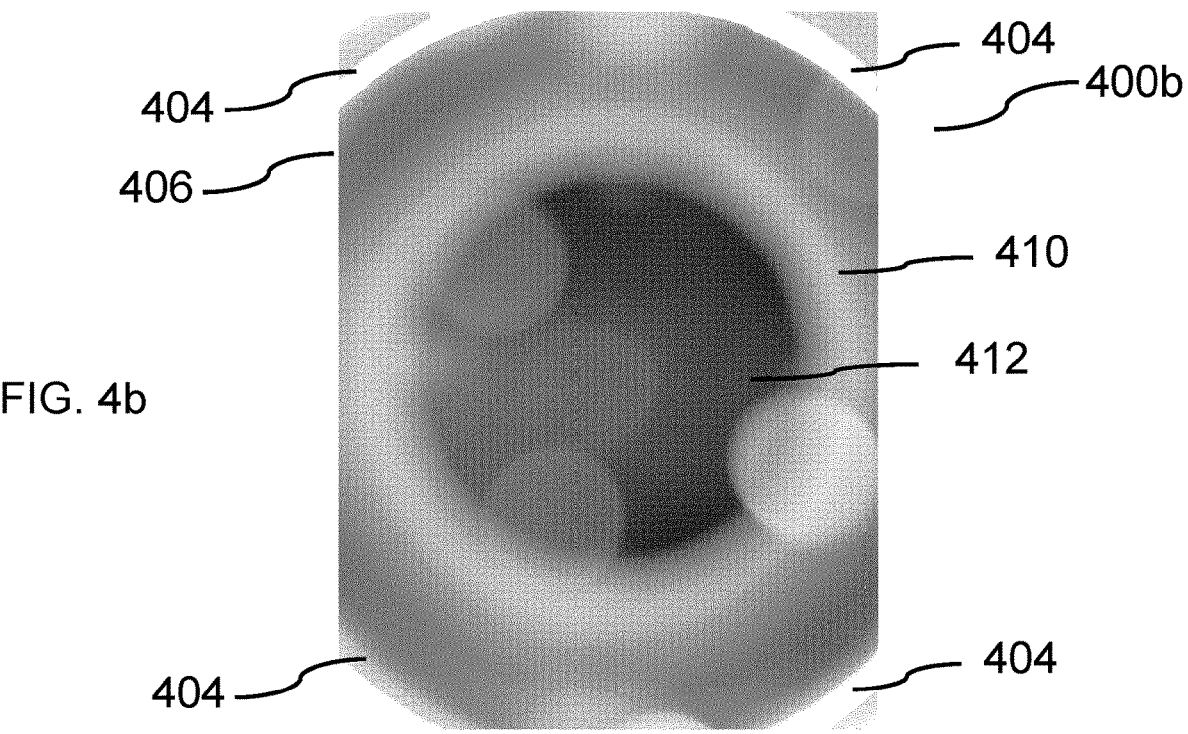

Method 200 then proceeds, initially capturing the image 400a shown in FIG. 4a. Image 400a may be an image captured as an algorithm runs at 30 frames per second and uses multiple high-performance computer vision techniques to extract and validate contrasting shape information, negate lighting variation and detect uniform visual artifacts (such as halo).

Image 400a includes interior portion 408, which may be a portion of an alignment present feature, and three arc portions 404.

Processing may occur in a few ways and be applied to image 400a and then 400b (after MA 102 is moved from the position in 400a to the position in 400b):
  (a) Halo processing (macro processing) followed by arc processing (micro processing).
    (i) Halo detection (macro processing) may be performed as the first processing step. Every camera frame may be converted to a LAB color space and then an algorithm may be used to determine multiple parameters of luminance uniformity in specific directions (for example top-to-bottom, right-to-left, bottom-to-top, left-to-right, top_right-to-bottom-left, bottom_right-to-top_left, bottom_left-to-top_right and top_left-to-bottom_right). Whenever a certain threshold is exceeded for a specific direction, guidance information is displayed on the screen (such as 502a/b and 504) to help correct the alignment and adjust, remove or focus the halo. As such, halo processing may continue until halo processing indicates MA 102 is in substantial alignment. Small center halo detection may also be employed, focusing on small halos that would be interior to 410.
    (ii) Arc detection (micro processing) may be performed as the next processing step, and may confirm halo processing. After processing the camera frame (image 400a or 400b) to extract shape information and remove lighting variation artifacts, a specifically designed computer vision model may be used to detect arc extrusions in all 4 corners of the image. The arc extrusions may be stored as 2D points in memory. Those 2D points are then used to calculate or locate the average center point of the 4 arcs, which is a direct correlation to the center point of the scanner lens itself. This center point is then compared to the "perfect" center point, which is the camera field of view center. Guidance information is then generated based on how far and which direction off-center the calculated point is. If thresholds are met and at least 2 arcs are being detected in the frame, then it is may be assume that the alignment is good enough to produce high quality skin images and the current position is deemed to be the aligned position (and an indicator, like the full circle 510, is displayed).
    (iii) Arc focus may also be used as part of macro or, more likely, micro processing. Arcs can be found, ideally in at least 2 corners of the current position image. The focus of each arc focus can be determined, which may provide a good indication of whether the current position is the aligned position.
    (iv) Applied to 400a, halo 410 may not be present. Processing then determines that an adjustment may be suggested. Applied to 400b, halo 410 may be acceptable after halo processing. Then the arcs are found and used to calculate a center (with x,y coordinates in the image, for example), which, upon checking, may be close enough to field of view center (with x, y coordinates in the image, for example) that there is alignment in 400b.

(b) Macro (as in (i) or (ii)) followed by micro processing.

(i) Macro alignment processing of image 400a indicates misalignment for example either because housing portion 402 is present in the image (as determined by noting the color and shape of such portion) or because there is a lack of a fourth arc portion (arc portions 404 are present in three quarters but not in the lower right portion, as 404b is missing—though perhaps as few as 2 arcs may be required to at least mathematically calculate the aperture center, even if only having 2 arcs makes it unlikely that the skin analysis device is in an aligned position). Given that housing portion 402 is in the bottom right section of image 408a the adjustment(s) are to move MA 102 down and to the left. Thus arrow 504 would be down, and ideally also to the left slightly. At the same time, adjustment message 506 may be shown as "Move down slightly" or "Move down and to the left slightly". Status indicator 508 may still show "confirm alignment" instead of "alignment confirmed" or the like.

(ii) Macro processing may consist of performing halo processing—one or more of i) looking for halo 410, ii) finding it, iii) finding that its shape and symmetry suggest an alignment position, and iv) determining its center (halo center) and whether the halo center is close to the field of view center. Halo processing may return a success if the halo exists and the halo center is close to the field of view center. However, in 400a there is no halo, which indicates no success (and rather a macro misalignment given there isn't even a halo 412) but rather a failure for halo processing. Such lack of halo may require some further processing to determine an adjustment—for example using the 3 arcs 404 or housing portion 402 may result in a similar "Move down and to the slightly" message. Halo processing, generally and as macro processing, may be effective because halo 412 is generally visible to some extent (even if it is not properly shaped given misalignment and is often less crisp then arcs 404 so are less reliable for highly accurate determination of the center of aperture 122) so if it is not then there is misalignment (whereas the absence of arcs may not mean misalignment if they are outside the field of view). In this way image 400a may be somewhat rare; if a user generally aligns aperture 122 over the camera, and/or aligns base contact 106 with alignment guide 302 there will normally be a halo.

(iii) Micro processing (which may be bottom surface micro processing, or arc detection micro processing, depending on the exact nature of the micro processing) may involve detecting the center of the circle defined by the bottom surface 122 of housing 110 and which may be used after halo processing has confirmed that the centers are at least close to aligned. The white arcs 404 in image 400b comprise a set of arc portions of the bottom surface of housing 110 and are detected and used, with geometrical formulas, to calculate the center of the circle that is defined by these arcs. That is then the center of aperture 122. Of course which parts of the bottom surface 122 are visible vary by MD 104, and the size of the arc is also variable, because different cameras can have different fields of view. To handle this, image 400b may be cropped such that all images are largely comparable and processing can be applied consistently, as opposed to having to adjust the processing for the different image sizes. For example, if one camera has a 32 mm field of view and another camera has a 28 mm field of view, it means the latter camera "sees" more of the image (wider angle), and the details will be smaller by about 12% (4/32). Cropping takes out the differences, by normalizing for field of view differences. In addition, in 400b we see halo 410 and subject portion 412, both of which indicate proper alignment as they are expected in an image and ought to be centered when in the aligned position (giving more possibilities for guiding features and performing calculations or locations of centers, and the like). Halo 410 may be used for macro alignment as the halo should be shape of housing aperture at the end of housing aperture that is remote from MD 104 and should be the color of the inner surface of housing aperture 122. Subject 412 can be part of the background—ie what may actually be in the image as seen through the aperture—though filtering and focusing on arcs 512 may render the lighting and content of what is seen through the lens and aperture less relevant.

In any approach to processing 400a, a user may then move MA 102 down and to the left, resulting in current image position 400b being taken. Macro processing may then indicate that MA 102 is at least close to the aligned position (for example using halo processing or other macro processing described herein), so that further micro processing is initiated.

Figure 6:
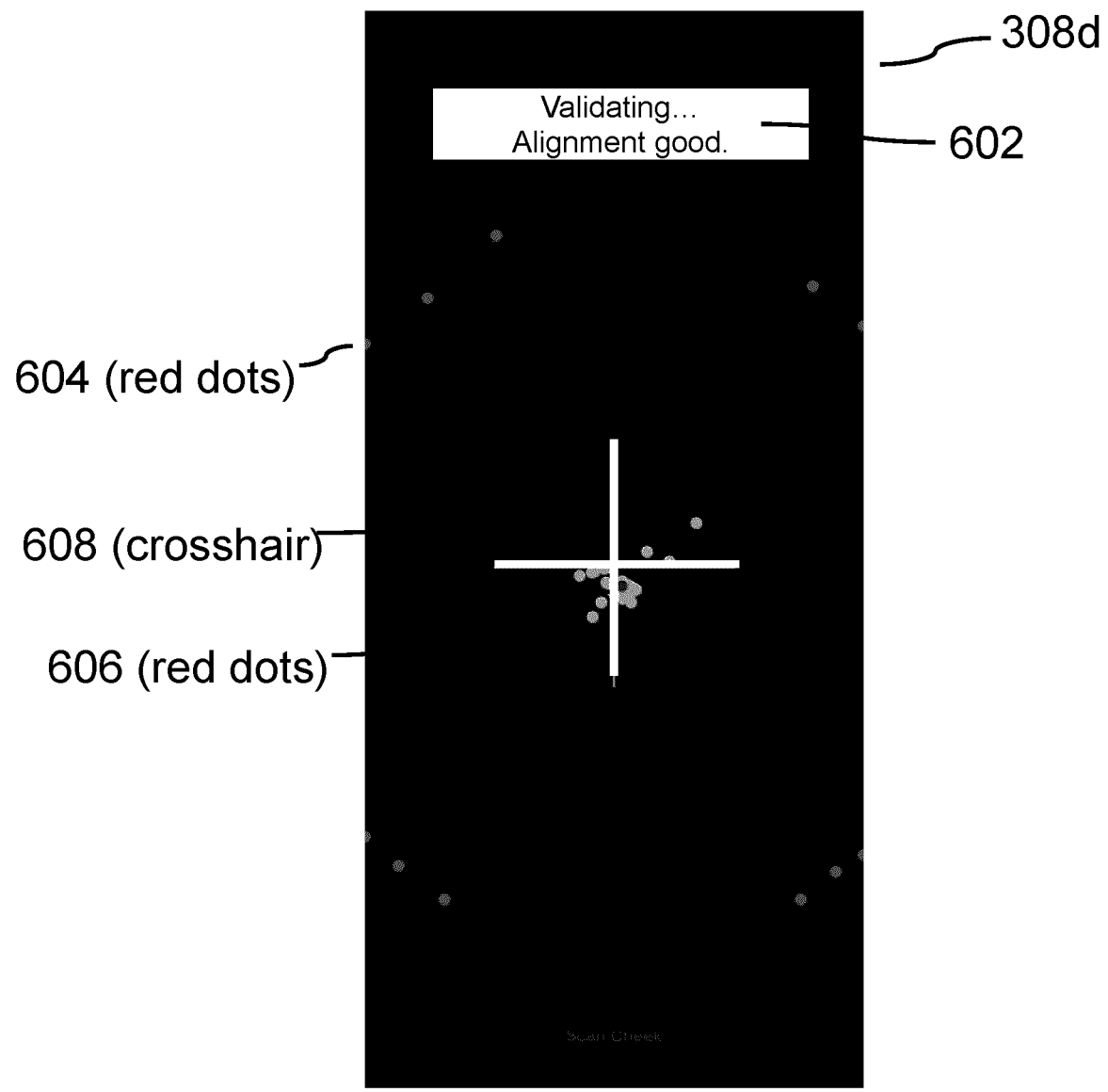

Although it may not be shown to a user, FIG. 6 shows a visual representation of some of the processing, for example of locating the housing aperture center. Field of view crosshair 608 is shown. Arc lines are defined in each corner of the image by arc points 604. Various aperture center points 606 are calculated based on geometrical formulas and the arc lines, for example using circumference and center calculations and arc points 604. For example, multiple sets of three points on the various arcs can be used to calculate the center of the circle using the general equation for circles $((x-x_c)^2+(y-y_c)^2-r^2=0)$ Provided that the various aperture center points 606 (for example the average of them) are within an acceptable distance from the center of crosshair 608 then the current position may be the aligned position.

Having identified MA 102 as being in the aligned position, the app proceeds to 210 of method 200 to communicate the success in reaching the aligned position. This may be via GUI 308c, with aligned position indicator 510 showing a formed circle around arcs 512a and 512b and adjustment message 506 indicating the alignment is good. Of course there are many ways that communication of alignment could be achieved, with elements of GUI 308c being only a few examples, other examples as may be described herein.

A user may then proceed to use the app to perform the functionality of MA 102. In the example shown in FIG. 1a, MA 102 may now be used to perform some form of analysis on a user, using a camera of MD 104.

FIGS. 1a and 1b are depictions of the device.

The device includes a clip or latch that has at least some ability to open and/or flex and grip the top and bottom sides of the smart device. The diameter of the space inside clip may be designed to "fit" many sizes of smart phones, with different diameters possibly being required (for example a small, a medium, a large, and a tablet size) for smart devices. "Fitting" may be such that the device is securely attached to the smart device, and in particular so that it is tight enough to enable the measurements and functionality described herein. A softer rubber or silicone material may be placed on the inside surface of the device, where it contacts the lens of the computing device, to absorb and block outside light. On one side of the clip arm may be a touch-sensitive guide or some other mark or opening (as described herein) to facilitate the alignment of the device to enable measurements and functionality.

The device further includes a component housing that houses all of the components of the device. Component housing may be made of the same material (and may be integral with) as the clip.

Inside component housing are the various components used to enable the measurements and functionality herein. These components may include a microprocessor, wireless transmission and receiving device, battery, charging port, polarization and other light filters, illumination devices, magnification lens, ultraviolet light source and measurement sensor, and a moisture sensor. Such components may be substantially similar to components described in PCT/CA2017/050503.

Figure 3:
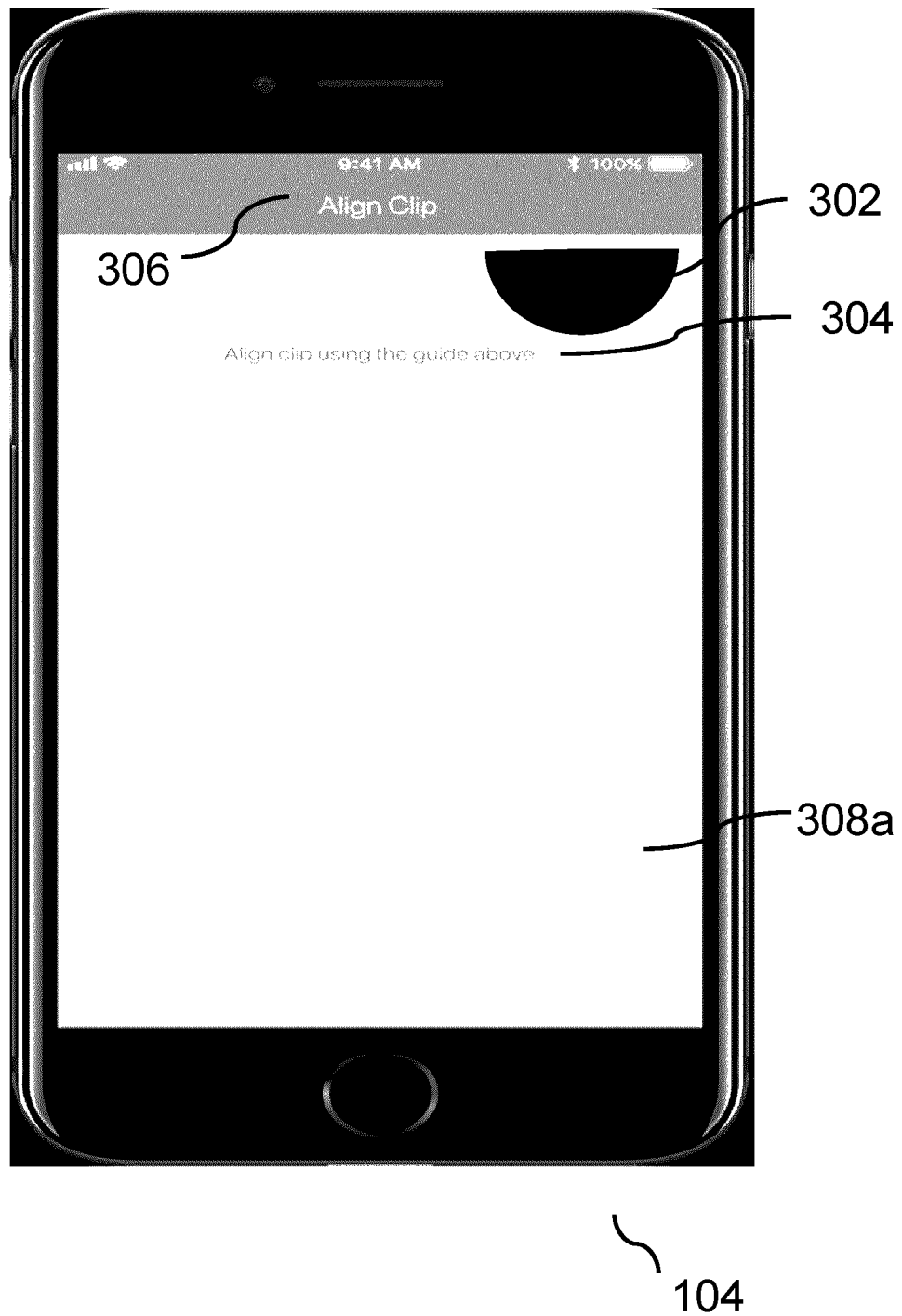
FIG. 3 illustrates a screenshot of an app for a mobile device according to an aspect of the present invention.

FIG. 3 shows template that appears in the software, to assist the user to position the device such that it is aligned in the horizontal and vertical dimensions with the smart device camera lens.

The Device works in the following way:
1) The device is clipped on a smart device. Different lengths of arms can be provided to accommodate different sizes of device (e.g., tablets, smart phones). To keep the round aperture (guide opening) in the clip parallel with the lens in the smart device, a rod is used on the opposite side that allows that side of the clip to achieve the appropriate angle, thus keeping the round aperture (guide opening) parallel with the camera lens.
2) The round aperture (guide opening) on the device is aligned with the built-in camera of the smart device. Alignment is in both the vertical and horizontal planes. To facilitate alignment, the device software will show an outline or template of the device on the screen of the smart device. The user aligns the device to match the template shown on the screen (screen guide). An alignment screen is particular to a particular smart device; alignment screens are much easier to design and amend than an entire hardware device. To facilitate alignment through software, one or more touch-sensitive pads may be used on one or both clip arms. The touch sensitive pad(s) will allow the software to determine exactly how the clip arm is oriented, in both the x and y planes, and at what angle it's rotated. This will allow the software to know where the clip arm is positioned, since the touch sensitive pad will interact with the touch sensitive screen. To facilitate alignment, the shape of the touch sensitive pad(s) match the size and shape of the end of the clip. This enables the user to easily align the end of the clip with a template shown on the smart device screen. Since each smart device model will have different mounting positions, the on-screen guide will change depending on the model of smart device being used. Users will be guided through audio and/or visual prompts on how to align the clip to the smart device.
3) The software can detect incorrect placement by measuring the out of focus areas, amount of vignette, and amount of extra light present in the image. This is accomplished through the lens of the camera, by analysis of the image taken by the camera lens. Machine vision algorithms that detect lack of sharpness and color shifts can be used to detect image degradation due to improper alignment of the lenses. These tools can also be used to assist users to align the clip with the lens of the smart device if the touch sensitive pad(s) do not make contact with a touch screen, or none exists.
4) It is activated by pressing the on/off switch, through software, or by using a skin detection system (such as a moisture or proximity sensor). It can also be activated when it touches the screen. The software detects that screen contact has been made through the touch sensitive pad(s), and then connects to the clip electronics.
5) One or more lights (in a variety of wavelengths) turn on and shine on the skin, including both linearly polarized, cross polarized, and non-polarized light.
6) One or more UV sensor(s) measures the amount of reflected light that bounces off the skin.
7) A warning light or message in a software application tells the user if the level of sunscreen at that point on the skin is sufficient. Other analyses include skin moisture, lines, wrinkles, pores, oil, elasticity, dark spots, and pollution level.
8) Usage data is collected and shared with the cosmetics or skin care manufacturer. Examples of collected data include but are not limited to: consumer sex, age, GPS location, weather at location, sunscreen application time, number of checks, number of times protection was exceeded, sunscreen products used, consumer feedback.
9) Product recommendations tailored to the consumer's skin type are displayed.

Reflection is measured by UV detection circuit, an example of which is the Vishay VEML6075. These work by converting UV light intensity into digital data. A sensor with a peak sensitivity of a similar wavelength of light to the source UV lights is selected. The sensor's output voltage determines the intensity of UV light that it detects. The Device is initially calibrated with a mirror (representing—100% light reflection, and in a dark room (representing—0% light reflection). The Thresholds described herein are then determined against several human skin examples. A manufacturer of sunscreen could adjust the Thresholds to levels they are comfortable with (e.g., a more cautious setting would alert the user to reapply or go indoors at a higher Reflection %).

It will be apparent to one of skill in the art that other configurations, materials etc may be used in any of the foregoing embodiments of the products, methods, and systems of this invention. It will be understood that the specification is illustrative of the present invention and that other embodiments within the spirit and scope of the invention will suggest themselves to those skilled in the art. All references cited herein are incorporated by reference.

The above-described embodiments of the present disclosure can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the concepts disclosed herein may be embodied as a non-transitory computer-readable medium (or multiple computer-readable media) (e.g., a computer memory, one or more floppy discs, compact discs, optical discs, magnetic tapes, flash memories, circuit configurations in Field Programmable Gate Arrays or other semiconductor devices, or other non-transitory, tangible computer storage medium) encoded with one or more programs that, when executed on one or more computers or other processors, perform methods that implement the various embodiments of the present disclosure discussed above. The computer-readable medium or media can be transportable, such that the program or programs stored thereon can be loaded onto one or more different computers or other processors to implement various aspects of the present disclosure as discussed above.

The terms "program" or "software" are used herein to refer to any type of computer code or set of computer-executable instructions that can be employed to program a computer or other processor to implement various aspects of the present disclosure as discussed above. Additionally, it should be appreciated that according to one aspect of this embodiment, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various features and aspects of the present disclosure may be used alone, in any combination of two or more, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the concepts disclosed herein may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

Several (or different) elements discussed below, and/or claimed, are described as being "coupled", "in communication with", or "configured to be in communication with". This terminology is intended to be non-limiting, and where appropriate, be interpreted to include without limitation, wired and wireless communication using any one or a plurality of a suitable protocols, as well as communication methods that are constantly maintained, are made on a periodic basis, and/or made or initiated on an as needed basis.

This written description uses examples to disclose the invention and also to enable any person skilled in the art to make and use the invention. The patentable scope of the invention is defined by the claims, and may include other examples that occur to those skilled in the art. Such other examples are within the scope of the claims if they have structural elements that do not differ from the literal language of the claims, or if they include equivalent structural elements with insubstantial differences from the literal language of the claims.

It may be appreciated that the assemblies and modules described above may be connected with each other as required to perform desired functions and tasks within the scope of persons of skill in the art to make such combinations and permutations without having to describe each and every one in explicit terms. There is no particular assembly or component that may be superior to any of the equivalents available to the person skilled in the art. There is no particular mode of practicing the disclosed subject matter that is superior to others, so long as the functions may be performed. It is believed that all the crucial aspects of the disclosed subject matter have been provided in this document. It is understood that the scope of the present invention is limited to the scope provided by the independent claim(s), and it is also understood that the scope of the present invention is not limited to: (i) the dependent claims, (ii) the detailed description of the non-limiting embodiments, (iii) the summary, (iv) the abstract, and/or (v) the description provided outside of this document (that is, outside of the instant application as filed, as prosecuted, and/or as granted). It is understood, for this document, that the phrase "includes" is equivalent to the word "comprising." The foregoing has outlined the non-limiting embodiments (examples). The description is made for particular non-limiting embodiments (examples). It is understood that the non-limiting embodiments are merely illustrative as examples.

What is claimed is:

1. A method for aligning a removably attachable skin analysis device, the skin analysis device comprising a housing that defines a housing aperture, the housing aperture comprising a housing aperture center and wherein the housing aperture is centered on a camera of the mobile device when the skin analysis device is in an aligned position, the housing further comprising skin analysis components that perform skin analysis, the method comprising:
   observing the skin analysis device in a current position on the mobile device;
   capturing, with the camera, a current position image, wherein the current position image comprises at least a portion of the housing aperture;
   processing the current position image to determine if the current position is the aligned position, wherein the processing comprises:
      performing halo processing, comprising determining one or more parameters of luminance uniformity in specific directions across the image, and if a threshold is exceeded for a specific direction, providing guidance information to help correct the current position; and
      if the halo processing is successful, using bottom surface micro processing to confirm the halo processing; and
   communicating a message from the processing.

2. The method of claim 1 wherein the camera has a field of view further comprising a field of view center and wherein the processing further comprises:
   locating the housing aperture center in the current position image;
   checking if the housing aperture center is centered on the field of view center in the current position image; and
   returning a success message if the housing aperture center is centered on the field of view center and a failure message if the housing aperture center is not centered on the field of view center.

3. The method of claim 2 wherein the housing aperture has a circular bottom surface, and a portion of the housing aperture in the current position images comprises a set of arc portions of the circular bottom surface and the locating comprises using the set of arc portions to determine the housing aperture center.

4. The method of claim 2 wherein the locating comprises performing halo processing.

5. The method of claim 3 wherein, if the housing aperture center is not centered on the field of view center in the current position image, the checking further comprises:
   computing an adjustment, using the located housing aperture center, to apply to the skin analysis device to move the skin analysis device from the current position to the aligned position; and
   wherein the failure message further comprises the adjustment.

6. The method of claim 5 wherein the calculating further comprises cropping the current position image to normalize for the camera's field of view.

7. The method of claim 5 where the processing further comprises:
   macro processing the current position image for a misalignment visual indicator; and
   if a misalignment visual indicator is found then returning a failure message that further comprises an adjustment to remove the misalignment visual indicators from the current position image.

8. The method of claim 2 further comprising displaying, on the screen of the mobile device, the message.

9. The method of claim 2 further comprising performing joint functionality, if the message is a success message.

10. The method of claim 6 wherein the alignment guide has a shape of a base connector of a mobile device accessory, wherein the base connector is to touch the screen in the location and orientation of the alignment guide and wherein the alignment guide's shape and location vary for each mobile device.

11. A method for preparing an alignment dependent mobile device accessory in an aligned position on a mobile device, the method comprising:
   observing the mobile device accessory in a current position, removably attached to the mobile device, the current position being an unknown alignment position;
   obtaining a current position image from a camera of the mobile device, the current position image comprising an image of at least a portion of the mobile device accessory in the current position;
   processing the current position image to determine if the current position is the aligned position, wherein the processing comprises:
   performing halo processing, comprising determining one or more parameters of luminance uniformity in specific directions across the image, and if a threshold is exceeded for a specific direction, providing guidance information to help correct the current position; and
   if the halo processing is successful, using bottom surface micro processing to confirm the halo processing; and
   communicating a message from the processing.

12. The method of claim 11 wherein if the current position is not the aligned position then the processing further comprises:
   calculating an adjustment to apply to the mobile device accessory to move the mobile device accessory from the current position to the aligned position and the message further comprises the adjustment.

13. The method of claim 12 wherein the processing further comprises:
   macro processing the current position image for a misalignment visual indicator; and
   if a misalignment visual indicator is found then the message further comprises an adjustment to remove the misalignment visual indicators from the current position image.

14. The method of claim 11 further comprising:
   showing, on a screen of the mobile device and before the observing, an alignment guide to assist in placing the mobile accessory in the current position.

15. A system for skin care analysis comprising:
   a skin analysis device, removably attachable to a mobile device, the skin analysis device comprising a housing that defines a housing aperture, the housing aperture comprising a housing aperture center and wherein the housing aperture is centered on a camera of the mobile device when the skin analysis device is in an aligned position, the housing further comprising skin analysis components that perform skin analysis; and
   the mobile device, further comprising a screen, an app, and a camera, the mobile device configured to:
      capture, with the camera, a current position image, wherein the current position image comprises at least a portion of the housing aperture;
      process the current position image to determine if the current position is the aligned position, wherein the processing comprises:

performing halo processing, comprising determining one or more parameters of luminance uniformity in specific directions across the image, and if a threshold is exceeded for a specific direction, providing guidance information to help correct the current position; and if the halo processing is successful, using bottom surface micro processing to confirm the halo processing; and communicate a message from the processing.

16. The system of claim 15 wherein the camera has a field of view further comprising a field of view center and wherein the processing further comprises:

locating the housing aperture center in the current position image;

checking if the housing aperture center is centered on the field of view center in the current position image; and returning a success message if the housing aperture center is centered on the field of view center and a failure message if the housing aperture center is not centered on the field of view center.

17. The system of claim 16 wherein the housing aperture has a circular bottom surface, and a portion of the housing aperture in the current position images comprises a set of arc portions of the circular bottom surface and the locating comprises using the set of arc portions to determine the housing aperture center.

18. The system of claim 17 wherein, if the housing aperture center is not centered on the field of view center in the current position image, the checking further comprises:

computing an adjustment, using the located housing aperture center, to apply to the skin analysis device to move the skin analysis device from the current position to the aligned position; and wherein the failure message further comprises the adjustment.

19. The system of claim 18 wherein the mobile device if further configured to crop the current position image to normalize for the camera's field of view.

* * * * *